United States Patent
Kroekenstoel et al.

(10) Patent No.: US 10,432,260 B1
(45) Date of Patent: Oct. 1, 2019

(54) CIRCUIT FOR INDUCTIVE COMMUNICATIONS WITH MULTIPLE BANDS

(71) Applicant: NXP B.V., Eindhoven (NL)

(72) Inventors: Dave Sebastiaan Kroekenstoel, Eindhoven (NL); Harry Neuteboom, Eindhoven (NL)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 16/252,843

(22) Filed: Jan. 21, 2019

(51) Int. Cl.
*H04B 5/00* (2006.01)
*A61B 5/00* (2006.01)
*H01Q 7/00* (2006.01)

(52) U.S. Cl.
CPC .......... *H04B 5/0012* (2013.01); *A61B 5/0031* (2013.01); *H01Q 7/005* (2013.01); *H04B 5/0081* (2013.01)

(58) Field of Classification Search
CPC .... H04B 5/0012; H04B 5/0081; H01Q 7/005; A61B 5/0031
USPC ........................................................ 455/41.1
See application file for complete search history.

(56) References Cited

U.S. PATENT DOCUMENTS

| 8,401,470 B2 | 3/2013 | Kroekenstoel et al. |
| 9,214,895 B2 * | 12/2015 | Shanan ............... H03B 5/1265 |
| 2018/0034513 A1 | 2/2018 | Dobyns |
| 2018/0035246 A1 | 2/2018 | Orescanin |
| 2018/0115050 A1 | 4/2018 | Yang et al. |

* cited by examiner

*Primary Examiner* — Eugene Yun

(57) ABSTRACT

Aspects are directed to a wireless communications approach in which a signal is conveyed via one of a number of particular frequency bands. In one example, a tank circuit includes an inductor and multiple capacitive circuits, and a driver circuit includes multiple buffers. One of the buffers is responsive to the input signal and another of the buffers is not responsive to the input signal. The driver circuit is configured to drive the tank circuit through a respective capacitive circuit while coupled to a respective buffer at a node of the inductor. A tuning-drive circuit drives the tank circuit for communicating in one band of a selectably-tunable frequency range. The tuning-drive circuit includes selectable (buffer and capacitor) portions configured to selectively couple to the node, for an overall drive strength and an overall tuning capacitance, and for tuning the tank circuit to a selected frequency band for wireless communication.

20 Claims, 4 Drawing Sheets

CIRCUIT FOR INDUCTIVE COMMUNICATIONS WITH MULTIPLE BANDS

OVERVIEW

Aspects of various embodiments are directed to apparatuses and methods for wireless communications using inductive circuitry for conveying data between two circuits via frequency modulation in one or more frequency bands.

In induction-based wireless technology, data communication is often effected from a transmitting circuit using an inductor, or transformer, to magnetically transfer the energy signal carrying the data to a receiving circuit (e.g., via any of a number of different modulation schemes such as phase/frequency-shift keying or PSK/FSK). In each of these inductively-based communications circuits, a signal driver may be used with a series connection to a capacitor for driving an RLC tank typically including a resistor, a capacitor and a coil/inductor. For effective transmission, the RLC tank needs to have a center frequency (resonance frequency) as centered for the frequency band in which the data-carrying signal is transmitted. The transmitting circuit also needs to drive the RLC tank at a proper transmit level which oftentimes uses a non-linear (or class-D) amplifier for realizing relatively low power dissipation and high power-conversion efficiency. For example, in a near-field magnetic-induction (NFMI) radio as used in personal health applications (e.g., hearing-aids), the coil (or inductor) transmits data over a short range (<30 cm for communicating data between two ears). To be able to have the best efficiency, a transmitter circuit can be implemented with an adjustable transmit-drive level so that the proper signal level is received at the receiving circuit, and each such adjustment affects the RLC tank due to a minimum amount of capacitance that is connected to the RLC tank via the driver. However, this can present a problem when a higher resonance frequency is needed than what is possible with the available minimum amount of driver-related capacitance. Consequently, the user wearing the hearing-aid experiences a degraded quality of the audio signal communicated between the transmitting and receiving circuit.

For a variety of applications including but not limited to personal health, these and other matters have presented challenges to efficiencies of wireless communications implementations using inductive circuitry.

SUMMARY

Various example embodiments are directed to issues such as those addressed above and/or others which may become apparent from the following disclosure concerning wireless communications such as those used in the transmission of data over relatively short ranges and/or applications related to personal health and welfare (e.g., biomedical implants) and in which a resonance frequency of a tank circuit can be affected by adjustment of a transmit level.

In certain example embodiments, aspects of the present disclosure also involve inductively-coupled communications of an input signal for wireless communications in a selected one of a plurality of frequency bands.

In another specific example embodiment, aspects of the invention disclosure are directed to an apparatus (e.g., device) for the wireless communication of a signal via the selection of a particular frequency band from many possible frequency bands. The device includes a tank circuit which contains an inductor and multiple capacitive circuits. In this example, a driver circuit, including multiple buffers, is included and with at least one of these buffers being responsive to the input signal and another of these buffers not being responsive to the input signal. The driver circuit is configured to drive the tank circuit through a respective capacitive circuit while coupled to a respective buffer at a node of the inductor. A tuning-drive circuit is configured to drive the tank circuit for communications operation in one band of a selectably tunable frequency range. The tuning-drive circuit includes selectable portions which contain at least one buffer and at least one capacitive circuit that may be configured to selectively couple to the node of the inductor for operation in parallel with the driver circuit. These selected portions contribute to an overall drive strength and an overall tuning capacitance, for tuning the tank circuit to a selected frequency band for wireless communication.

In more specific example embodiments, aspects of the invention disclosure are directed to a near-field magnetic-induction (NFMI) radio configured for the wireless communication of a signal via the selection of one particular frequency band of many possible frequency bands. The device includes a tank circuit, which includes an inductor and multiple capacitive circuits. Further included in the device is a driver circuit, composed of multiple buffers. At least one of the buffers is responsive to the input signal while at least is not responsive to the input signal. The driver circuit is configured to drive the tank circuit through a respective capacitive circuit while coupled to a respective buffer at a node of the inductor. Also included in the device is a tuning-drive circuit configured to drive the tank circuit to operate in one band of a selectably tunable frequency range. The tuning-drive circuit includes selectable portions which contain at least one buffer and at least one capacitive circuit that can be configured to selectively couple to the node of the inductor for operation in parallel with the driver circuit. These selected portions contribute to an overall drive strength and an overall tuning capacitance, tuning the tank circuit to a selected frequency band for wireless communication.

In other specific example embodiments, the selectable circuitry is configured to enable the driver circuit to provide a known drive strength for a given center frequency corresponding to a particular frequency band. Portions of the tuning-drive circuit may be selectively disabled to configure the driver circuit to provide a different drive strength.

The above discussion/summary is not intended to describe each embodiment or every implementation of the present disclosure. The figures and detailed description that follow also exemplify various embodiments.

BRIEF DESCRIPTION OF FIGURES

Various example embodiments may be more completely understood in consideration of the following detailed description in connection with the accompanying drawings, in which.

Figure 1:
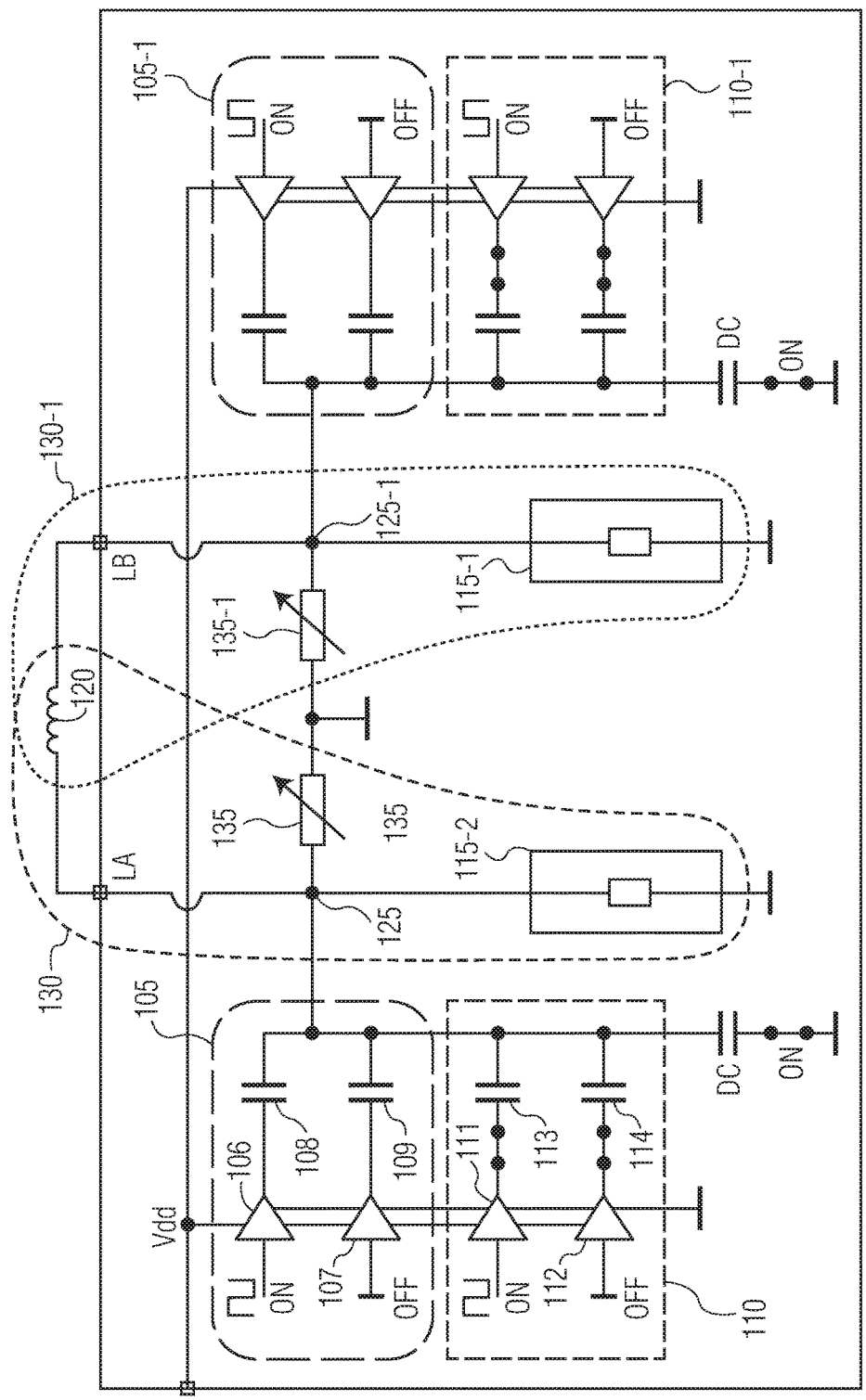
FIG. 1 is a circuit-level diagram illustrating an example device for wireless communications, in accordance with the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems, and methods directed to the wireless communication of an input signal through the selection of one frequency band. In certain implementations, aspects of the present disclosure have been shown to be beneficial when used in the context of personal health applications (e.g., biomedical implants). In some embodiments, a transmitter circuit can have its transmit-drive level and/or overall capacitance tuned so the proper signal level is received, in turn increasing fidelity of signal transmission. While not necessarily so limited, various aspects may be appreciated through the following discussion of non-limiting examples which use exemplary contexts.

Accordingly, in the following description, various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

In specific embodiments, aspects of the present disclosure are directed to a wireless communications device for wirelessly transmitting an input signal by coupling to external devices/circuitry via the selection of one of multiple frequency bands. This wireless communications device includes a tank circuit, a driver circuit, and a tuning-drive circuit. The tank circuit wirelessly communicates a signal via the selection of a particular frequency band from many possible frequency bands. The device includes a tank circuit which includes an inductor and multiple capacitive circuits. Further included in the device is a driver circuit, composed of multiple buffers. The driver circuit is configured to drive the tank circuit through a respective capacitive circuit while coupled to a respective buffer at a node of the inductor. A tuning-drive circuit is configured to drive the tank circuit for communications operation in one band of a selectably tunable frequency range. The tuning-drive circuit includes selectable portions which contain at least one buffer and at least one capacitive circuit that may be configured to selectively couple to the node of the inductor for operation in parallel with the driver circuit. These selected portions contribute to an overall drive strength and an overall tuning capacitance, tuning the tank circuit to a selected frequency band for wireless communication.

In more-specific example embodiments, certain selectable portions of the tuning-drive circuit enable the driver circuit to be configured to provide a known drive strength for a given center frequency corresponding to a particular frequency band. Disabling certain of the selectable portions of the tuning-drive circuit can configure the driver circuit to provide a different drive strength, less than the known drive strength, for a different center frequency corresponding to another frequency band. Depending on the embodiment and/or application, the circuit is implemented with capacitance in series with the driver connected to the RLC tank. In this manner, the resonance frequency does not change when the transmit level changes. When switching in more driver sections, the transmit level increases. This switching can be achieved, for example, by using a controller to selectably disconnect buffer inputs from fixed reference level(s) and concurrently activating the buffer(s). The amount of capacitance that is connected via the active driver(s) yields a certain minimum amount of capacitance that is connected to and affecting the RLC tank. When a resonance frequency is needed which is higher than what is possible with this minimum amount of capacitance, the number of driver sections (and effective level of drive) connected to the RLC tank can be selected, such that a larger freedom is provided in terms of resonance frequency while at the same time providing the ability to tune the resonance frequency. Note further that, in such example embodiments, the maximum drive strength is determined by the ratio between switching driver capacitance and capacitance that is not switching.

In accordance with the present disclosure, additional example embodiments are directed to a tuning capacitive circuit coupled between the node and a power rail. When in such an arrangement, the tuning capacitive circuit is configured to affect the resonance frequency of the tank circuit while the driver circuit drives the tank circuit. A second tuning capacitive circuit may be selectively coupled between the node and a power rail and configured to affect another resonance frequency of the tank circuit while both the tuning-drive circuit and the driver circuit cooperatively drive the tank circuit. Furthermore, when coupled between a node and a power rail, the tuning capacitive circuit may be configured to affect a resonance frequency of the tank circuit while the driver circuit drives the RLC tank circuit.

In other example embodiments, at least one of a first and a second tuning capacitive circuit is selectively controlled to affect the resonance frequency of the tank circuit by adding or subtracting capacitance at the tank circuit. Upon certain of the selectable portions of circuitry being activated, the first driver is configured to provide a known drive strength for a given center frequency corresponding to one band, as tuned via the first tuning capacitive circuit. Furthermore, when certain other portions of the selectable circuitry are disabled, the driver circuit is configured to provide a different drive strength, less than the known drive strength, for a different center frequency corresponding to another one of the multiple available frequency bands.

Aspects of the present disclosure are directed to additional embodiments wherein the overall tuning capacitance is established when a first and a second tuning capacitive circuits are coupled to the node. Overall drive strength is established collectively by the buffers, the driver circuit, and at least one additional buffer of the tuning-drive circuit when coupled to the node.

In additional embodiments, aspects of the present disclosure are directed to devices which include a controller circuit configured to selectively connect and/or disconnect at least one capacitive circuit and at least one buffer circuit within the tuning-drive circuit. This controller circuit can also be configured to selectively connect and/or disconnect at least one tuning capacitive circuit, in turn affecting resonance of the tank circuit. Additionally, the controller circuit and the selected tuning capacitive circuitry may be coupled between the node and a power rail, configured to affect resonance associated with the tank circuit when driven by the tuning-drive circuit. The selected tuning capacitive circuitry is configured to provide parasitic capacitance while the controller is configured to selectively alter the parasitic capacitance of the selected tuning capacitive circuitry at different times and/or to enable the tuning-drive circuit.

According to additional example embodiments, either and/or both of the driver circuit and the tuning-drive circuit can be configured to provide a linear gain when fed by a modulated carrier signal within a selected one of multiple different frequency bands. Also, either and/or both of the driver circuit and the tuning-drive circuit can be configured to act as an electronic switch, in turn providing a nonlinear gain by switching back and forth between supply rails when fed a modulated carrier signal within a selected one of the multiple different frequency bands.

In more specific example embodiments, aspects of the present disclosure are directed to a near-field magnetic-induction (NMFI) radio for wirelessly transmitting an input signal by NMFI radio communications via the selection of one of multiple frequency bands. This NMFI radio includes a tank circuit, a driver circuit, and a tuning-drive circuit. The tank circuit includes an inductor and multiple capacitive circuits. The inductor can be configured to couple to a circuit external to the device, while the capacitive circuits can be configured to drive the tank circuit through a respective capacitive circuit to ensure operation of the device in one band of a selectably tunable frequency range. Included in the driver circuit is a set of buffers. At least one of the buffers is responsive to the input signal while at least one other buffer is not responsive to the input signal. Finally, the tuning-drive circuit includes selectable portions containing at least one buffer and at least one capacitive circuit configured to selectively couple to the node of the inductor for operation in parallel with the driver circuit. When selected and in operation, the selected portions of the tunable circuitry cause the tank circuit to be tuned to a selected frequency band by contributing, along with the first driver, an overall drive strength. Furthermore, the selected portions contribute to an overall tuning capacitance for the wireless communication of the tank circuit.

As may be implemented within the above-mentioned example of a biomedical implant and in accordance with various embodiments, FIG. 1 depicts a wireless communications device including a first driver circuit 105 and a tuning-drive circuit 110 that are connected, along with an inductor 120, to a common node 125. A tank circuit 130 (which includes the capacitive tuning circuitry 115, the inductor 120, and a tunable resistance 130) passes signals for the wireless communications to the common node 125 via the inductor 120. The tank circuit 130 is configurable, via a control circuit (such as exemplified in FIG. 3), to select one of a number of available frequency bands used to convey such data wirelessly (e.g., to external receiving circuity via frequency modulation in one or more frequency bands). The first driver circuit 105 and the tuning-drive circuit 110 are used in parallel to set an overall drive strength and tuning capacitance for the tank circuit 130 for the selected frequency band.

In a specific embodiment, the first driver circuit 105 uses one or more buffer circuits 106 in an activated state (ON) to drive the tank circuit 130 (for the associated capacitive tuning circuit 115) while one or more of the buffer circuits 107 is in an inactive (OFF) state. Capacitors 108 and 109 couple the outputs of buffers 106 and 107 to the common node 125 to contribute to an overall drive strength of the tank circuit 130. Upon being configured and arranged to do so, tuning-drive circuit 110 uses one or more buffer circuits 111 in an activated state (ON) to drive the tank circuit 130 (for the associated capacitive tuning circuit 115) while one or more of the buffer circuits 112 is in an inactive (OFF) state. Capacitors 113 and 114 couple the outputs of buffers 111 and 112 to the common node 125, enabling tuning-drive circuit 110 to further contribute to the overall drive strength and tuning capacitance of the tank circuit 130.

As is apparent, the exemplified circuity shown in FIG. 1 is configured so as to be symmetrical with the above-discussed circuitry on the left side of FIG. 1, corresponding to similarly-configured circuitry on the right side of FIG. 1 as depicted by the suffixed reference numerals (e.g., 105 being symmetrical with 105-1, 110 with 110-1, 115 with 115-1, etc.).

Figure 2:
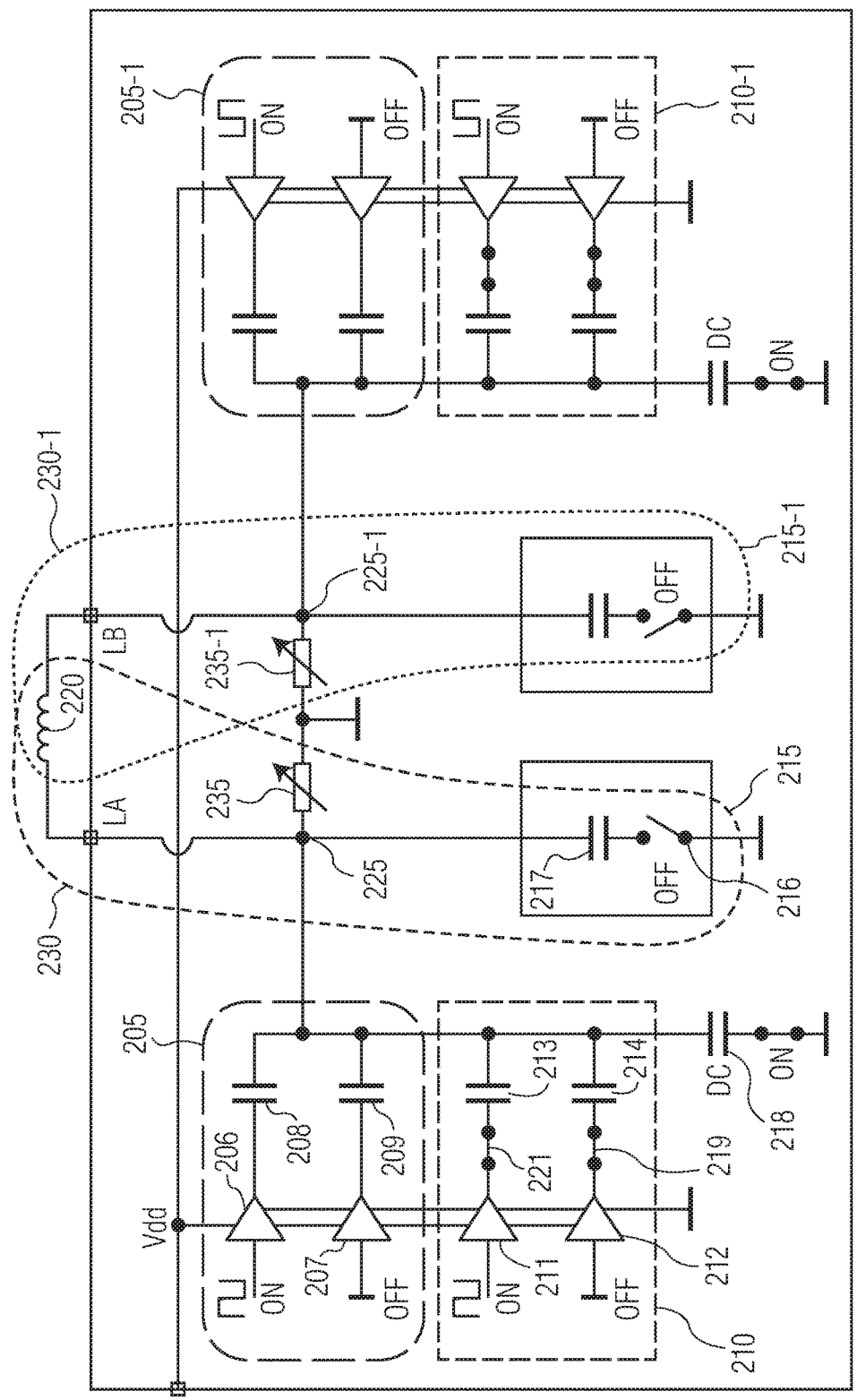
FIG. 2 is a circuit-level diagram illustrating an example device for wireless communications, depicting tunable capacitive circuitry consistent with FIG. 1, also in accordance with the present disclosure.

Also directed to the above-mentioned example embodiments and expanding upon FIG. 1, FIG. 2 depicts a wireless communications device including a first driver circuit 205 and a tuning-drive circuit 210 that are connected, along with an inductor 220, to a common node 225. A tank circuit 230 (which includes the capacitive tuning circuitry 215, the inductor 220, and a tunable resistance 230) passes signals for the wireless communications to the common node 225 via the inductor 220. The tank circuit 230 is configurable, via a control circuit (such as exemplified in FIG. 3), to select one of a number of available frequency bands used to convey such data wirelessly (e.g., to an external receiving circuity via frequency modulation in one or more frequency bands). The first driver circuit 205 and the tuning-drive circuit 210 are used in parallel to set an overall drive strength and tuning capacitance for the tank circuit 230 for the selected frequency band.

In a specific embodiment, the first driver circuit 205 uses one or more buffer circuits 206 in an activated state (ON) to drive the tank circuit 230 (for the associated capacitive tuning circuit 217, assuming switch 216 is ON) while one or more of the buffer circuits 207 is in an inactive (OFF) state. Capacitors 208 and 209 couple the outputs of buffers 206 and 207 to the common node 225 to contribute to an overall drive strength of the tank circuit 230. Upon being configured and arranged to do so, tuning-drive circuit 210 uses one or more buffer circuits 211 in an activated state (ON) to drive the tank circuit 230 (for the associated capacitive tuning circuit 215) while one or more of the buffer circuits 212 is in an inactive (OFF) state. Capacitors 213 and 214 couple the outputs of buffers 211 and 212 to the common node 225, enabling tuning-drive circuit 210 to further contribute to the overall drive strength and tuning capacitance of the tank circuit 230.

Various embodiments are directed toward mitigating or reducing overall capacitance connected to the inductor 220. In certain implementations, the amount of capacitance from the inductor 220 toward ground is increased and the drive strength is reduced to change the resonance frequency of the tank circuit 230. Tuning capacitance can be reduced and/or minimized, in the event the overall tuning capacitance being provided by the tuning capacitive circuitry 215 is sufficient, by disabling tuning-drive circuit 210 (e.g., turning off switch 218). Referring to FIG. 2, switch 216 may be turned OFF, causing the capacitive tuning circuitry 215 to contribute nothing toward the overall tuning capacitance of the tank circuit 230. As further illustrated in FIG. 2, switches 218, 219, and 221 may be turned ON. Switch 218 being ON enables the tuning-drive circuit 210 to contribute to the overall drive strength and tuning capacitance of the tank circuit 230. Switch 219 being ON allows the signal from buffer 212 to be coupled through capacitor 214 to the common node 225, while switch 221 being ON allows the signal from buffer 211 to be coupled through capacitor 213 to the common node 225.

Tuning-drive circuit 210 can be selectably configurable to work in parallel with the first driver circuit 205 to drive the tank circuit 230 through a respective capacitive circuit 217 of a set of capacitive tuning circuits 215. The respective tuning capacitive circuit 217 and switch 216 are configured to allow at least one of the first driver circuit 205 and/or the tuning-drive circuit 210 to provide a gain, which may be linear or non-linear, as dictated by the switching back and forth between supply rails when a modulated carrier signal within a set of frequency bands.

As is apparent, the exemplified circuity shown in FIG. 2 is configured so as to be symmetrical with the above-discussed circuitry on left side of FIG. 2 corresponding to similarly-configured circuitry on the right side of FIG. 2 as depicted by the suffixed reference numerals (e.g., 205 being symmetrical with 205-1, 210 with 210-1, 215 with 215-1, etc).

Figure 3:
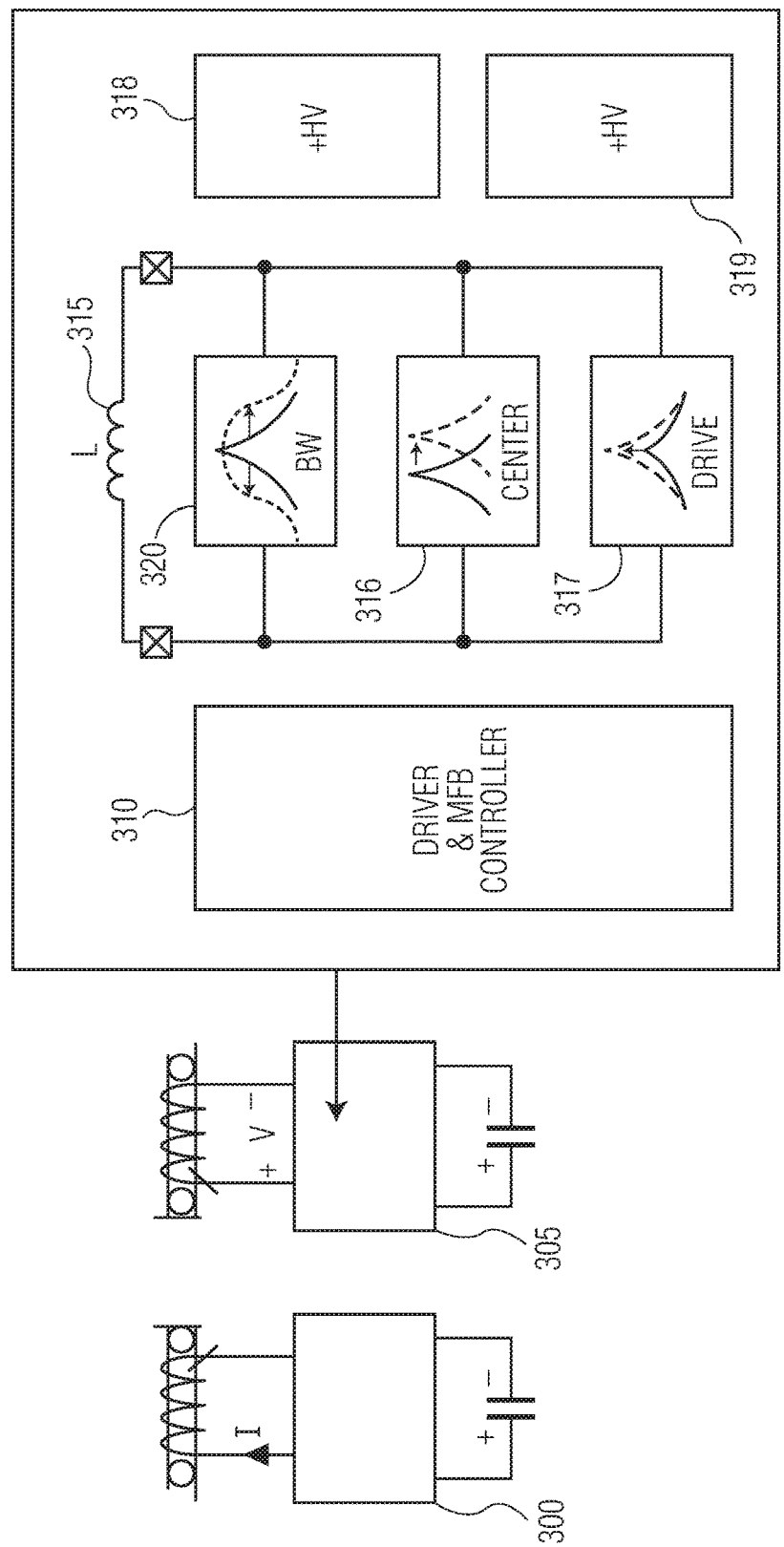
FIG. 3 is a system-level diagram illustrating a wireless communications device, in accordance with the present disclosure; and Each of FIGS. 4A and 4B is a diagram, related to specific embodiments and in accordance with the present disclosure, showing interaction between circuit aspects as used in connection with a biomedical implant.

Depicted in FIG. 3 is a wireless communications device, as may be implemented in a manner consistent with the above-mentioned example embodiments, in accordance with the present disclosure for communicating data between transmitting circuit 300 and receiving circuit 305. Through inductive communications enabled through an inductor 315, transmitting circuit 300 and receiving circuit 305 exchange data, for example, via frequency and/or phase modulation.

Adjacent the receiving circuit 305 is an example block diagram illustrating features of the receiving circuit 305 and how it can be implemented. As shown, the receiving circuit 305 includes a driver and multiple frequency band (MFB) controller 310 that enables/disables various driver and tuning circuitry used to configure characteristics, such as resonance frequency depicted as being tunable via block 316, drive strength depicted as being tunable at block 317, and bandwidth depicted as a tunable aspect 320. The multiple frequency band controller 310 can also be configured to dynamically control high voltage switches 318, 319 in operational use of the device. The receiving circuit 305 can be configured to select one of a plurality of different frequency bands, at which time it receives data from transmitting circuit 300 via frequency modulation.

In a detailed/experimental embodiment, which may be implemented in a manner consistent with the above embodiments and the instant disclosure, the above-discussed circuit shown in connection with FIG. 3 is used with the wireless connectivity provided via a carrier frequency in the Megahertz range (e.g., one Megahertz to 50 Megahertz). In one specific example, data being conveyed is provided via carrier frequency centered at 10.6 MHz and with a bandwidth of 400 kHz. To this end, the corresponding RLC tank circuitry includes equivalent impedance values of 9 Ohms, 3.8 microHenries (uH), and 50-70 picoFarads respectively for R, L and C. As an example, a battery (e.g., Zn-air battery) can be used as a power source for the integrated circuitry (IC chips) shown including the buffers.

Figure 4A:
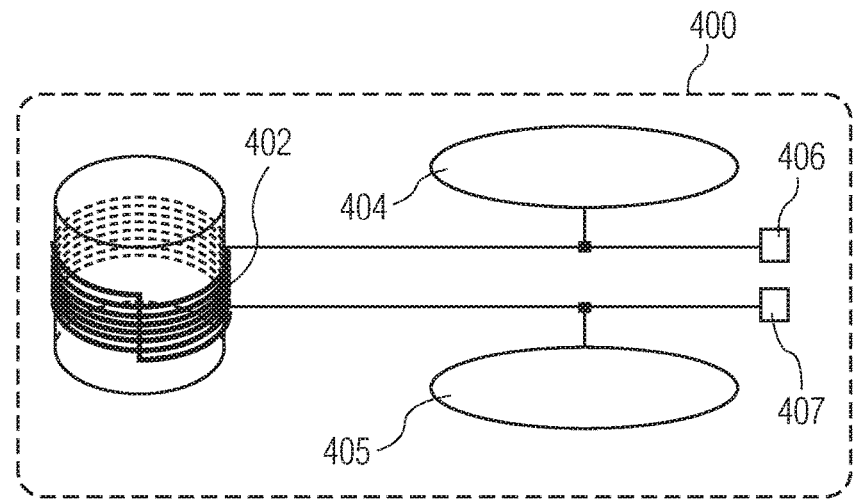
Figure 4B:
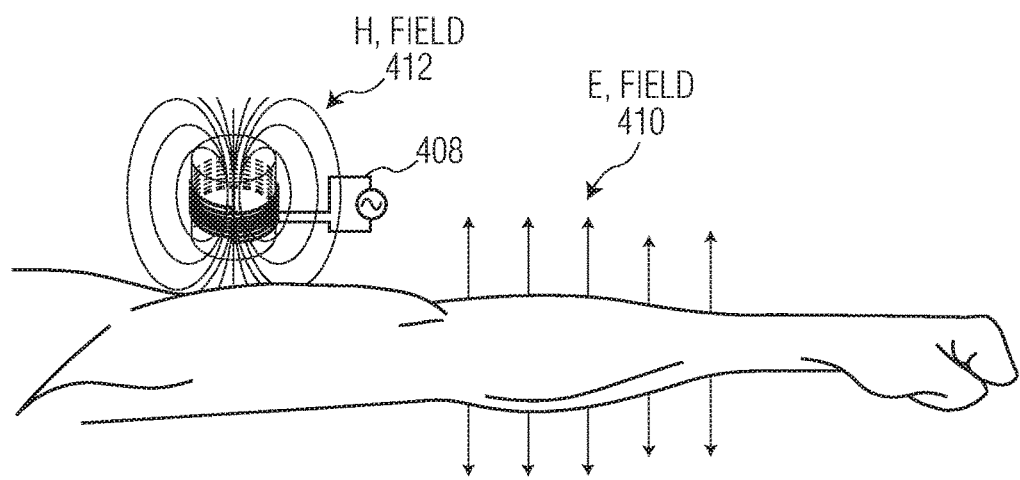

As yet another more-specific type of embodiment, corresponding to and/or useful with a biomedical implant or a device used close to the human body, FIG. 4A illustrates a near-field magnetic-induction (NMFI) antenna 400, comprising a coil (inductor) 402 connected to conducting plates 404 and 405, terminating in feeding connections 406 and 407. Such an NMFI antenna 400 may be used to communicate with a device implanted in, for example, a human arm as depicted in FIG. 4B. To establish communication between NMFI antenna 400 and the biomedical device (e.g., a transmitting and/or receiving device consistent with the circuitry depicted in FIG. 3), an electromotive force (e.g., voltage) 408 is applied to feeding connections 406 and 407 of the NMFI antenna 400. In certain embodiments, such a biomedical device may be implanted in or used in sufficient proximity to the human arm (e.g., sufficiently close to and/or as part of physiological-sensor circuitry such as a heart pulse monitor for relaying sensed physiological parameters or metrics).

As depicted in FIG. 4B, once applied, voltage 408 generates and/or induces electric field 410 and magnetic field 412. According to the principles of electromagnetic induction, a changing current, the production of which may result from the application of a voltage 408 through a wire (coil 402), creates a magnetic field 412 around the wire (coil 402). In turn, the induced magnetic field 412 magnetically couples the coil 402 of NMFI antenna 400 with the coil/inductor of the device (which may be implemented in accordance with the circuitry depicted in FIG. 3) implanted in the human arm, establishing inductive (wireless) communication between the devices.

In additional example embodiments, buffers are used in connection with driver circuitry (similar to the arrangements shown in FIGS. 1, 2 and 3) with the buffers being configured not to respond to an input signal such as by biasing (or tying) an input port of the buffer(s) to a fixed reference level (e.g., connecting to a supply rail such as Vcc, common, ground, etc).

According to additional example embodiments, either and/or both of the driver circuit and the tuning-drive circuit can be configured to provide a linear gain when fed by a modulated carrier signal within a selected one of multiple different frequency bands. Also, either and/or both of the driver circuit and the tuning-drive circuit can be configured to act as an electronic switch, in turn providing a nonlinear gain by switching back and forth between supply rails when fed a modulated carrier signal within a selected one of the multiple different frequency bands.

Terms to exemplify orientation, such as upper/lower, left/right, top/bottom above/below, and first/second may be used herein to refer to relative positions of elements as shown in the figures. It should be understood that the terminology is used for notational convenience only and that in actual use the disclosed structures may be oriented different from the orientation shown in the figures. Thus, the terms should not be construed in a limiting manner.

The skilled artisan would recognize that various terminology as used in the Specification (including claims) connote a plain meaning in the art unless otherwise indicated. As examples, the Specification describes and/or illustrates aspects useful for implementing the claimed disclosure by way of various circuits or circuitry which may be illustrated as or using terms such as blocks, modules, device, system, unit, controller, and/or other circuit-type depictions. Such circuits or circuitry are used together with other elements to exemplify how certain embodiments may be carried out in the form or structures, steps, functions, operations, activities, etc. As another example, where the Specification may make reference to a "first [type of structure]", a "second [type of structure]", etc., where the [type of structure] might be replaced with terms such as ["circuit", "circuitry" and others], the adjectives "first" and "second" are not used to connote any description of the structure or to provide any substantive meaning; rather, such adjectives are merely used for English-language antecedence to differentiate one such similarly-named structure from another similarly-named structure (e.g., "first circuit configured to convert . . . " is interpreted as "circuit configured to convert . . . ").

Based upon the above discussion and illustrations, those skilled in the art will readily recognize that various modifications and changes may be made to the various embodiments without strictly following the exemplary embodiments and applications illustrated and described herein. For example, methods as exemplified in the Figures may involve steps carried out in various orders, with one or more aspects of the embodiments herein retained, or may involve fewer or more steps. Such modifications do not depart from the true spirit and scope of various aspects of the disclosure, including aspects set forth in the

What is claimed is:

1. An apparatus comprising:
   a tank circuit, including an inductor and a first plurality of capacitors, configured for wireless communication of a signal, derived from an input signal, via a selectable one of a plurality of different frequency bands;
   a first driver, including a plurality of buffers of which at least one is responsive to the input signal and of which at least one other is not responsive to the input signal, configured to drive the tank circuit through a respective capacitor of the first plurality of capacitors, while the tank circuit is coupled to a respective buffer of the plurality of buffers and to a node of the inductor;
   a tuning-drive circuit configured to drive the tank circuit for communications operation in one band of, and selectably from, the plurality of different frequency bands; and
   the tuning-drive circuit including selectable portions each having at least one additional buffer and at least one capacitor configured to be selectively coupled to the node of the inductor for operation in parallel with the first driver, and when selected and in operation, the selected portions cause the tank circuit to be tuned to a selected one of the plurality of different frequency bands by contributing, with the first driver, to an overall drive strength and to an overall tuning capacitance for the wireless communication for the tank circuit being tuned to the selectable one of a plurality of different frequency bands.

2. The apparatus of claim 1, wherein by enabling certain circuitry of the selectable portions of the tuning-drive circuit, the first driver is configured to provide a known drive strength for a given center frequency corresponding to the one band and by disabling other circuitry of the selectable portions of the tuning-drive circuit, the first driver is configured to provide a different drive strength, less than the known drive strength, for a different center frequency corresponding to the other band.

3. The apparatus of claim 1, further including: a first tuning capacitive circuit coupled between the node and a power rail and configured to affect a resonance frequency of the tank circuit while the first driver drives the tank circuit; and a second tuning capacitive circuit selectively coupled between the node and a power rail and configured to affect another resonance frequency of the tank circuit while both the tuning-drive circuit and the first driver cooperatively drive the tank circuit.

4. The apparatus of claim 1, further including: a first tuning capacitive circuit coupled between the node and a power rail and configured to affect a resonance frequency of the tank circuit and including a second tuning capacitive circuit selectively coupled between the node and a power rail and configured to affect another resonance frequency of the tank circuit, wherein at least one of the first tuning capacitive circuit and the second tuning capacitive circuit is selectively controlled to affect a resonance frequency of the tank circuit by effectively adding or subtracting capacitance at the tank circuit.

5. The apparatus of claim 1, further including a first tuning capacitive circuit coupled between the node and a power rail and including a second tuning capacitive circuit selectively coupled between the node and a power rail, wherein certain circuitry of the selectable portions is activated, the first driver is configured to provide a known drive strength for a given center frequency corresponding to the one band, as tuned by contribution of the first tuning capacitive circuit, and wherein when certain other circuitry of the selectable portions is activated the tuning-drive circuit is configured to provide a different drive strength, less than the known drive strength, for a different center frequency corresponding to another one of the bands.

6. The apparatus of claim 1, further comprising a controller circuit configured to selectively cause connection and/or disconnection, in the tuning-drive circuit, of at least one of said at least one capacitor and said at least one additional buffer.

7. The apparatus of claim 1, further comprising: at least one tuning capacitor configured to affect a resonance associated with the tank circuit; and a controller circuit configured to selectively cause connection and/or disconnection of said at least one tuning capacitor.

8. The apparatus of claim 1, further comprising: a controller circuit; and at least one tuning capacitor coupled between the node and a power rail and configured to affect a resonance associated with the tank circuit when being driven by the tuning-drive circuit, wherein said at least one tuning capacitor is configured to provide a parasitic capacitance, and the controller circuit is configured to selectively alter the parasitic capacitance at different times and to enable the tuning-drive circuit.

9. The apparatus of claim 1, wherein said at least one of the plurality of buffers of the first driver, which is not configured to be responsive to the input signal, has an input which is at a fixed reference level due to being biased to or towards one of a supply voltage and ground.

10. The apparatus of claim 1, wherein the inductor is configured and arranged to magnetically couple with a circuit which is external to the apparatus.

11. The apparatus of claim 1, wherein at least one of the first driver and the tuning-drive circuit is configured as an electronic switch configured to provide a gain which is nonlinear by switching back and forth between supply rails, while being fed by a modulated carrier signal within one of the plurality of different frequency bands.

12. The apparatus of claim 1, wherein at least one of the first driver and the tuning-drive circuit is configured to provide a linear gain, while being fed by a modulated carrier signal within one of the plurality of different frequency bands.

13. The apparatus of claim 1, further including a first tuning capacitive circuit coupled between the node and a power rail and including a second tuning capacitive circuit selectively coupled between the node and a power rail, wherein the overall tuning capacitance is established collectively by the first tuning capacitive circuit while coupled to the node, by the second tuning capacitive circuit while coupled to the node, and by the first plurality of capacitors while coupled to the node, and the overall drive strength is established collectively by the plurality of buffers of the first driver while coupled to the node and by said at least one additional buffer of the tuning-drive circuit while coupled to the node.

14. The apparatus of claim 1, further including at least one housing configured to fit in and/or around an ear while containing the first driver and the tuning-drive circuit.

15. A near-field magnetic-induction radio, comprising:
a tank circuit, including an inductor and a first plurality of capacitors, configured for wireless communication of a signal by near-field magnetic-induction radio communication, derived from an input signal, via a selectable one of a plurality of different frequency bands;
a first driver, including a plurality of buffers of which at least one is responsive to the input signal and of which at least one other is not responsive to the input signal, configured to drive the tank circuit through a respective capacitor of the first plurality of capacitors, while the tank circuit is coupled to a respective buffer of the plurality of buffers and to a node of the inductor;
a tuning-drive circuit configured to drive the tank circuit for communications operation in one band of, and selectably from, the plurality of different frequency bands;
the tuning-drive circuit including selectable portions each having at least one additional buffer and at least one capacitor configured to be selectively coupled to the node of the inductor for operation in parallel with the first driver, and when selected and in operation, the selected portions cause the tank circuit to be tuned to a selected one of the plurality of different frequency bands by contributing, with the first driver, to an overall drive strength and to an overall tuning capacitance for the wireless communication for the tank circuit being tuned to the selectable one of a plurality of different frequency bands; and
a controller circuit configured to selectively cause connection and/or disconnection, in the tuning-drive circuit, of at least one of said at least one capacitor and said at least one additional buffer.

16. A circuit-implemented method for wireless communication using a tank circuit, including an inductor and a first plurality of capacitors, the method comprising:
via a first driver, including a plurality of buffers of which at least one is responsive to an input signal and of which at least one other is not responsive to the input signal, driving the tank circuit through a respective capacitor of the first plurality of capacitors, while the tank circuit is coupled to a respective buffer of the plurality of buffers and to a node of the inductor;
driving the tank circuit for communications operation in one band selected from a plurality of different frequency bands, wherein a tuning-drive circuit includes selectable portions each having at least one additional buffer and at least one capacitor configured to be selectively coupled to the node of the inductor for operation in parallel with the first driver; and
operating the first driver and the tank circuit by activating the selected portions to cause the tank circuit to be tuned to a selected one of the plurality of different frequency bands by contributing, with the first driver, to an overall drive strength and to an overall tuning capacitance for the wireless communication for the tank circuit being tuned to the selectable one of a plurality of different frequency bands.

17. The method of claim 16, using at least one tuning capacitor to affect a resonance associated with the tank circuit; and using a controller circuit to selectively cause connection and/or disconnection of said at least one tuning capacitor.

18. The method of claim 17, wherein said at least one tuning capacitor is configured to provide a parasitic capacitance, and the controller circuit is configured to selectively alter the parasitic capacitance at different times and to enable the tuning-drive circuit.

19. The method of claim 16, wherein said at least one of the plurality of buffers of the first driver, which is not configured to be responsive to the input signal, has an input which is at a fixed reference level due to being biased towards one of a supply voltage and ground.

20. The method of claim 16, further including using the tuning-drive circuit for wireless communication in proximity of a physiological-related metrics of a human.

* * * * *